(12) United States Patent
Wurst (10) Patent No.: US 10,196,602 B2
(45) Date of Patent: Feb. 5, 2019

(54) BIOMATERIAL BASED ON A HYDROPHILIC POLYMERIC CARRIER

(75) Inventor: Helmut Wurst, Pfullingen (DE)

(73) Assignee: NMI NATURWISSENSCHAFTLICHES UND MEDIZINISCHES INSTITUT AN DER UNIVERSITAET TUEBINGEN, Reutlingen (DE)

(*) Notice: Subject to any disclaimer, the term of this patent is extended or adjusted under 35 U.S.C. 154(b) by 539 days.

(21) Appl. No.: 12/655,983

(22) Filed: Jan. 11, 2010

(65) Prior Publication Data

US 2010/0184223 A1 Jul. 22, 2010

Related U.S. Application Data

(63) Continuation of application No. PCT/EP2008/005643, filed on Jul. 10, 2008.

(30) Foreign Application Priority Data

Jul. 13, 2007 (DE) .................. 10 2007 034 580

(51) Int. Cl.
   *C12N 5/00* (2006.01)
   *A61L 27/22* (2006.01)
   *A61L 27/38* (2006.01)

(52) U.S. Cl.
   CPC .......... *C12N 5/0068* (2013.01); *A61L 27/227* (2013.01); *A61L 27/38* (2013.01); *C12N 2533/30* (2013.01); *C12N 2533/50* (2013.01); *C12N 2537/10* (2013.01)

(58) Field of Classification Search
   None
   See application file for complete search history.

(56) References Cited

U.S. PATENT DOCUMENTS

| | | | |
|---|---|---|---|
| 5,916,585 A * | 6/1999 | Cook et al. ................. | 424/426 |
| 6,861,404 B1 * | 3/2005 | Cohen et al. ................ | 514/6.9 |
| 2002/0049498 A1 | 2/2002 | Yuksel et al. | |
| 2002/0032463 A1 * | 3/2002 | Cruise et al. ............... | 606/214 |
| 2002/0076443 A1 * | 6/2002 | Stein et al. ................. | 424/486 |
| 2002/0193812 A1 * | 12/2002 | Patel ............... | A61B 17/12022 606/151 |
| 2003/0040760 A1 | 2/2003 | Hnojewyj et al. | |
| 2006/0089719 A1 | 4/2006 | Trieu | |
| 2006/0255503 A1 | 11/2006 | Higham et al. | |
| 2007/0049688 A1 * | 3/2007 | Kozlowski et al. ......... | 525/54.1 |
| 2010/0184223 A1 | 7/2010 | Wurst | |

FOREIGN PATENT DOCUMENTS

| EP | 0 844 252 | 5/1998 |
|---|---|---|
| EP | 1263327 | 8/2005 |
| JP | 11-322799 | 11/1999 |
| WO | WO-99/07416 | 2/1999 |
| WO | WO-00/37124 | 6/2000 |
| WO | WO-01/60335 | 8/2001 |
| WO | WO-01/66017 | 9/2001 |
| WO | WO-2009/010232 | 1/2009 |

OTHER PUBLICATIONS

Teramura et al. Islet-Encapsulation in Ultra-Thin Layer-By-Layer Membranes of Poly)Vinyl Alcohol) Anchored to Poly(Ethylene Glucol)-Lipids in the Cell Membrane; Biomaterials, vol. 28 (2007) pp. 4818-4825.*
Anonymous. Hydrogel definition, TheFreeDictionary.com (2014) downloaded from: http://medical-dictionary.thefreedictionary.com/hydrogel on Nov. 10, 2014.*
Elbert et al. Protein Delivery From Materials Formed by Self-Selective Conjugate Addition Reactions; Journal of Controlled Release, vol. 76 (2001) pp. 11-25.*
International Preliminary Report on Patentability (Translation) for PCT/EP2008/005643, 8 pages.
Anseth et al., Journal of Controlled Release (2002) 78:199-209.
Hersel et al., Biomaterials (2003) 24:4385-4415.
Levesque and Shoichet, Bioconjugate Chem. (2007) 18:874-885.
Lutolf and Hubbell, Nature Biotechnology (2005) 23:47-55.
Manecke and Vogt, Biochimie. (1980) 62:603-613.
Nie et al., Journal of Controlled Release (2007) 122:287-296.
Pratt et al., Biotechnology and Bioengineering (2004) 86:27-36.
International Search Report for PCT/EP2008/005643, dated Dec. 9, 2008, 3 pages.
Shalaby et al., "Enzyme-Degradable Hydrogels", ACS symposium series (1991) pp. 484-492.
Ganey et al., "Disc chondrocyte transplantation in a canine model: a treatment for degenerated or damaged intervertebral disc," Spine (2003) 28(23):2609-2620.
International Preliminary Report on Patentability in PCT/EP2009/000542, dated Mar. 3, 2010, 14 pages (English translation included).
International Search Report for PCT/EP2009/000542, dated May 19, 2009, 7 pages (English translation included).
Kawasaki et al., "Hyaluronic acid enhances proliferation and chondroitin sulfate synthesis in cultured chondrocytes embedded in collagen gels," J Cell Physiol (1999) 179(2):142-148.
Restriction Requirement in U.S. Appl. No. 12/844,750, dated Sep. 17, 2012, 8 pages.

(Continued)

*Primary Examiner* — Scott Long
*Assistant Examiner* — Paul C Martin
(74) *Attorney, Agent, or Firm* — Rimon, P.C.

(57) ABSTRACT

The present invention relates to a biomaterial for cell or tissue culture, based on a polymeric carrier, which contains at least one crosslinkable hydrophilic polymer. The polymer is functionalized with groups that are selected from maleimide, vinylsulfonic, acrylate, alkyl halide, azirine, pyridyl, thionitrobenzene acid groups, or arylating groups. The invention relates further to a method of production of said biomaterial, and the use of particular functionalizing groups for the production of a biomaterial for the cultivation of tissue and/or cells. The biomaterial can have biofactors that exert a particular action on cells.

22 Claims, 3 Drawing Sheets
(3 of 3 Drawing Sheet(s) Filed in Color)
Specification includes a Sequence Listing.

(56) References Cited

OTHER PUBLICATIONS

Response to Restriction Requirement in U.S. Appl. No. 12/844,750, dated Oct. 17, 2012, 5 pages.
Non-Final Office Action in U.S. Appl. No. 12/844,750, dated Dec. 14, 2012, 6 pages.
Response to Non-Final Office Action in U.S. Appl. No. 12/844,750, dated Mar. 13, 2013, 11 pages.
Final Office Action in U.S. Appl. No. 12/844,750, dated Apr. 1, 2013, 7 pages.
Request for Continued Examination in U.S. Appl. No. 12/844,750, dated Sep. 30, 2013, 9 pages.
Non-Final Office Action in U.S. Appl. No. 12/844,750, dated Oct. 22, 2014, 10 pages.

* cited by examiner

```
                    SEQUENCE LISTING

<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: ACETYLATION

<400> SEQUENCE: 1

Lys Gly Leu Gln Gly Cys Gly Leu Gln Gly Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: ACETYLATION

<400> SEQUENCE: 2

Lys Gly Gly Leu Gln Gly Gly Lys
1               5

<210> SEQ ID NO 3
<211> LENGTH: 15
<212> TYPE: PRT
<213> ORGANISM: Artificial Sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: bAla

<400> SEQUENCE: 3

Ala Gly Cys Gly Tyr Gly Arg Gly Asp Ser Pro Gly Ser Gly Cys
1               5                   10                  15
```

BIOMATERIAL BASED ON A HYDROPHILIC POLYMERIC CARRIER

CROSS-REFERENCE TO RELATED APPLICATIONS

This application is a continuation of co-pending International Patent Application PCT/EP2008/005643 filed on Jul. 10, 2008, and designating the United States, which was not published in English, and claims priority of German Patent Application DE 10 2007 034 580.3, filed on Jul. 13, 2007. The contents of these applications are herein incorporated by reference in their entireties.

BACKGROUND OF THE INVENTION

The present invention relates to a biomaterial for the culture of cells and/or tissue consisting of cells, based on a polymeric carrier, which contains at least one crosslinked hydrophilic polymer.

Said biomaterials are used in the prior art for example as so-called drug-release materials, as implants, as tissue-forming matrixes or as materials for cell culture, and are often also called "hydrogels". These biomaterials are usually employed for therapeutic purposes or for biological basic research, because owing to their variable biophysical and biochemical properties they represent valuable tools in regenerative medicine and in "tissue engineering", and in general cell culture.

With these biomaterials it is therefore possible for example to restore the structure and function of degenerated or damaged tissue, when they are loaded with cells and then implanted, and thus subsequently promote tissue morphogenesis, or if, not loaded with cells, they are implanted in places where, through the growing-in of cells and optionally their differentiation, they promote the formation of new tissue in situ.

As already mentioned, another main application of biomaterials based on natural or synthetic materials is in analytical cell culture applications, by which for example the mechanism of action of biofactors on cells can be investigated.

Various biomaterials based on natural or artificial materials with various properties are known in the prior art, which generally, depending on the desired field of application, are characterized by adequate mechanical stability, elasticity, and resistance to degradation, and above all are nontoxic. Preparations of collagen I are frequently used materials of natural origin. This hydrophilic protein contains regions that react with cells, for example adhesion signals, signals for the proteolytic cleavage of collagen I, or for cell differentiation. These signals and the three-dimensional nature of cultivation contribute to cells in these collagen gels behaving more naturally than in conventional two-dimensional culture on surfaces of culture vessels.

For a better understanding of the functioning of these signals, it is necessary to use biomaterials in which the type and number of signal groups can be controlled, i.e., a biomaterial which does not damage the cells and at first does not carry any signals and is therefore neutral to cells, and which can be modified with signal groups.

In the prior art, see, e.g., Hersel, et al., *Biomaterials* 24 (2003) 4385-4415; and Lutolf and Hubbell, *Nature Biotechnology*, 23 (2005) 47-66, as a general rule polyethylene glycol—hereinafter generally abbreviated with PEG—is used as such a polymer that is neutral to cells, as it is nontoxic, it is not bound by cells and is hydrophilic. However, because linear PEG can only be modified at its two ends, and because for the formation of a crosslinked gel at least one reactant must bear at least three reactive groups, on the one hand peptides, which bear at least three reactive groups, are used for crosslinking, or alternatively branched PEG is used, which for example possesses four modifiable ends.

However, the polymers or hydrogels known in the prior art have the disadvantage that the production/isolation of the peptides used for crosslinking is difficult and expensive, and so too is the production of branched PEG. Another disadvantage is that the production of gels from reactants with three or four reactive groups per molecule requires very careful work, because for gel formation all the reactants must be in the correct proportions.

The approaches known in the prior art are therefore disadvantageous for the development of reagents for cell and tissue culture.

SUMMARY OF THE INVENTION

A problem to be solved by the present invention is therefore to provide a biomaterial with which the disadvantages of the biomaterials known in the prior art can be overcome.

This problem is solved by providing a biomaterial that is based on a polymeric carrier, which contains at least one crosslinked hydrophilic polymer, the polymer being functionalized with groups that are selected from maleimide, vinylsulfonic, acrylate, alkyl halide, azirine, pyridyl, thionitrobenzene acid groups, or arylating groups.

The problem on which the invention is based is solved completely in this way.

The biomaterial according to the invention provides a polymer that has very many modifiable groups, and at the same time, in comparison with branched PEG, can be produced very inexpensively.

With the biomaterial according to the invention, hydrogels can be prepared inexpensively, which on the one hand can be used in the culture of cells and investigation thereof with respect to reaction to biofactors, or on the other hand optionally also in the cultivation of tissue, either ex vivo by colonization with cells and implantation in a tissue that is to be regenerated, or in situ by providing a matrix into which cells can migrate.

Furthermore, there is also the possibility of using the biomaterial or the hydrogel as a "drug-release" biomaterial, i.e., as a material from which active substances are released in situ. These active substances can for example be medicinal products, pharmaceuticals or other natural or synthetic active substances, i.e., substances that exert a particular action on the tissue or cells surrounding the biomaterial.

In the present invention, "biomaterial" shall mean any natural or synthetic material that is suitable for the production of matrixes or gels, which can be used for the culture of cells/tissues ex vivo or in vivo.

"Functionalized" and "functionalize" shall, in the present invention, mean any finalized or closed process by which the polymer—for example by adding-on of groups to the polymer—is endowed with a function that it does not normally possess. The resultant "functionalized polymer" is then called a "biomaterial".

"Tissue" shall, in the present invention, mean any group of identically differentiated or differently differentiated cells. In a multicellular organism, tissues can together fulfill a circumscribed range of tasks and/or can form the specific building material for organs, in direct contrast to the mere aggregation of undifferentiated or only temporarily differentiated individual cells.

"Cell or tissue culture" shall, in the present invention, mean any application in which cells can, for the purpose of multiplication or differentiation, or the synthesis of cellular and extracellular components, be applied or can migrate onto the biomaterial, and optionally form a tissue.

The biomaterial is then "cell-neutral", which in the present invention shall mean on the one hand literally that the biomaterial displays "neutral" behavior with respect to cells, and therefore does not have any effect on the cells, and does not trigger any reaction in the cells. With these materials, the cells do not bind "of their own accord" to the polymer, but optionally only after modification of the polymer with appropriate groups.

The biomaterial thus prepared can then, depending on the particular application, be specially modified with biofactors. Cells can be introduced into the biomaterial, can interact with the biofactors coupled to it, and can then be investigated. This permits selective investigation of particular biofactors and their action on cells.

With the biomaterials known in the prior art, based for example on collagen, this was not possible, as these already react with the cells directly and can trigger cell reactions, which makes selective investigation of biofactors or their mechanisms of action on cells impossible.

The substances used for the functionalization of the polymer are, for the biomaterial according to the invention, selected from maleimide, vinylsulfonic, acrylate, alkyl halide, azirine, pyridyl, thionitrobenzene acid groups, or arylating groups. Via these groups, in their turn for example biofactors can be applied to the polymer, and then cells can bind to these. The polymer is then combined with cells and is transformed by a crosslinking agent into a three-dimensional hydrophilic network. On the other hand, however, the cells can also be incorporated in the biomaterial without biofactors, for example purely for cultivation, so that in this embodiment the cells are added directly to the functionalized polymer, which is then crosslinked in the presence of the cells.

The experiments described hereinafter demonstrate the adhesion of cells to gel components and the cultivation of cells in the gel, as well as the modification of the biomaterial with peptides.

According to one aspect of the invention, the polymer of the biomaterial is selected from polyvinyl alcohol (PVA), serum albumin (e.g., bovine), pullulan, polyvinylpyrrolidone, methyl cellulose, amylose, amylopectin, glycogen, or mixtures thereof.

Of these, in particular functionalized polyvinyl alcohol and functionalized bovine serum albumin are preferred. With these last two materials, experiments on coupling of peptides to the polymer and on cultivation of cells in the biomaterial were successful.

The use of the aforementioned hydrophilic, cell-neutral, functionalized polymers for the culture of cells and/or tissues is not known or made obvious in the prior art. Admittedly, for antibody production, maleimide-functionalized bovine serum albumin was used for coupling peptides to BSA, but its use for the culture of cells and/or tissues was neither demonstrated nor proposed.

Moreover, the use of maleimide-functionalized polyvinyl alcohol is known in the prior art, see Manecke and Vogt, *Biochimie* 62 (1980): 603-613, but only for the immobilization of enzymes, without any mention or disclosure of use for cell or tissue culture.

That maleimide-functionalized polymers, or polymers that are functionalized with one of the other aforementioned groups, are suitable for use as biomaterial for the culture of cells and/or tissues, was unexpected and not obvious. The experiments on which the application is based show for the first time that the biomaterials according to the invention provide an efficient tool for cell and/or tissue culture, and also offer excellent properties for the investigation of biofactors, or for their reaction on/with cells.

Therefore, according to another aspect of the invention, the biomaterial also has at least one biofactor, and in particular if the biofactor has at least one thiol group, via which the biofactor is bound covalently to maleimide groups of the polymer.

"Biofactor" shall, in the present invention, mean any natural or synthetic substance that can have an influence on cells, or that can exert reactions on/in cells. This influence can be restricted to certain cells and certain conditions, and the substance would still be regarded as a "biofactor". The chemical nature of the substances designated as "biofactors" herein is not limited to a particular class of, e.g., compounds, but instead can include any natural or synthetic substance which, by its nature and/or in modified form, exerts any action on biological cells.

"Signal groups" shall, in the present invention, mean any part of a biofactor, by which reaction of cells to the biofactors is triggered.

The term "cells" shall hereinafter comprise all cells that can be cultivated with the present biomaterial, and includes in particular eukaryotic cells, in particular mammalian cells such as human and animal cells.

According to another aspect of the invention the biofactor is selected from peptides, proteins, nucleic acids, organic active substances, apoptosis-inducing active substances, adhesion-promoting active substances, growth-inhibiting active substances, anti-inflammatory active substances, receptor agonists and receptor antagonists, or mixtures thereof.

This embodiment has the advantage that various factors can be specially selected, whose action on cells is in fact known, but whose specific action in a three-dimensional culture milieu has yet to be discovered.

In particular it is preferred if the biofactor is selected from: proteins of the extracellular matrix, cell surface proteins, antibodies, growth factors, sugars, lectins, carbohydrates, cytokines, DNA, RNA, siRNA, aptamers, and fragments thereof that are relevant to binding or action, or mixtures thereof.

The extracellular matrix (intercellular substance, ECM) is the portion of the tissue that is secreted by cells into the intercellular space, i.e., the space between the cells. The ECM therefore represents the totality of all macromolecules that are located outside of the plasma membrane of cells in tissues and organs. The extracellular matrix largely consists of various proteins, in particular collagens, and glycoproteins, in particular laminins, vitronectin, fibronectin, or of certain polysaccharides, the glycosaminoglycans.

The term "fragments thereof relevant to binding or action" shall hereinafter mean parts/segments of the aforementioned biofactors, which, although possibly not the complete biofactor is used, in themselves still exert the same or almost the same or at least similar reaction or action on cells, as the complete biofactor. Reaction can mean simply the binding of/to cells, but can also mean a cell's reaction to the binding, subsequent to the binding, such as for example the induction of certain reaction pathways in the cells, which can lead to production/release of certain substances by the cells, or else to transformation or differentiation of the cells.

According to another aspect of the invention, the peptide has a sequence that is selected from SEQ ID NO:1 (peptide "HW1"), SEQ ID NO:2 (peptide "HW2") or SEQ ID NO:9 (peptide "HW9") from the appended sequence listing. The amino acid sequence 6-11 in HW9 is an adhesion sequence from human fibronectin, but it also occurs in some other organisms. The flanking sequences are not of natural origin.

The invention relates moreover to a method for the production of a biomaterial for cell/tissue culture applications, which has the following consecutive steps:
- a) preparation of a hydrophilic polymer,
- b) functionalization of the polymer from step a) with a substance that is selected from maleimide, vinylsulfonic, acrylic acid, alkyl halide, azirine, pyridyl, thionitrobenzene acid groups, or arylating groups, and
- c) addition of a crosslinking agent for crosslinking the polymer modified in step b).

The method according to the invention has the advantage that it can be used for producing biomaterials inexpensively, which are neutral with respect to cells, and which provide a simple and reliable tool with which for example cells can be investigated or cultivated.

According to another aspect of the invention, the method additionally has step a)':
- a) amination of the polymer.

This method is used in particular in the production of maleimide functionalized PVA, whereas for example BSA (bovine serum albumin) does not require amination prior to functionalization.

Thus, according to another aspect of the invention, the method additionally has step b)' after step b):
- b)' addition of and incubation with biofactors and/or cells, in particular mammalian cells.

In this embodiment, advantageously either first biofactors and then cells are added onto the functionalized polymer, so that the biofactors can bind covalently to the functional groups, and the cells to the biofactors. On the other hand there is the possibility of adding the cells without covalently bound biofactors to the polymer, resulting for example in a biomaterial only for cell culture, without investigation of the reactions of biofactors to the cells.

According to another aspect of the invention the polymer is selected from polyvinyl alcohol, serum albumin, in particular bovine serum albumin, dextran, pullulan, polyvinylpyrrolidone, methyl cellulose, amylose, amylopectin, glycogen, or mixtures thereof.

These embodiments have the advantage that substances can be employed that have been demonstrated to have neutral behavior with respect to cells.

Moreover, and according to another aspect of the invention, the biofactor is selected from peptides, proteins, nucleic acids, organic active substances, apoptosis-inducing active substances, adhesion-promoting active substances, growth-inhibiting active substances, anti-inflammatory active substances, receptor agonists and receptor antagonists, and in particular from proteins of the extracellular matrix, cell surface proteins, antibodies, growth factors, sugars, lectins, carbohydrates, cytokines, DNA, RNA, siRNA, aptamers, and fragments thereof relevant to binding or action, or mixtures thereof.

According to another aspect of the method according to the invention, the crosslinking agent in step c) is selected from Dithio-PEG or SH-modified dextran.

These crosslinking agents were used successfully in experiments on which the invention is based. A further advantage is that both substances have been described sufficiently in the prior art and have been tested for any undesirable side reactions.

In the method according to the invention it is preferred if a biomaterial according to the invention, as described, is produced.

The invention relates further to a method for modification and/or functionalization of hydrophilic polymers, wherein maleimide, vinylsulfone, acrylate, alkyl halide, azirine, pyridyl, or thionitrobenzene acid are used, for the production of a biomaterial for cell culture applications, and in particular the use of the mentioned substances for the production of a biomaterial according to the invention as previously described.

With the present application, a novel method is provided, by means of which hydrophilic polymers can be generated which comprise functionalized groups, and the thus generated functionalized polymers can be used for the production of a biomaterial, which is suitable for cell and/or tissue culture.

Of course, for precise investigation and analysis of cells, these should desirably be such that the biomaterial can be degraded by in each case specifically suitable substances. The substance to be used depends on the crosslinking agent and/or polymer that is used, so that for example when using dextran as crosslinking agent or as polymer, dextranases can be used for degradation.

Other advantages can be seen from the description and the appended figures.

Of course, the features presented above and others still to be explained below can be used not only in the combinations stated in each case, but also in other combinations or alone, while remaining within the scope of the present invention.

BRIEF DESCRIPTION OF THE FIGURES

The patent or application file contains at least one drawing executed in color. Copies of this patent or patent application publication with color drawings will be provided by the Office upon request and payment of the necessary fee.

Examples of the invention are presented in the figures and are explained in more detail in the subsequent description. The figures show:

FIGS. 2A-F confocal laser scanning micrographs of MDCK cysts after 15 days in the PVA gel for visualization of the lumen; FIG. 2C shows a phase-contrast photograph and FIG. 2D shows an overlay of C, D and E.

FIGS. 3A-B the results of cultivation of mesenchymal stem cells in PVA and BSA gels (calcein/propidium iodide staining); with FIG. 3A showing the cultivation in a BSA gel, and FIG. 3B showing the cultivation in PVA gel.

DESCRIPTION OF PREFERRED EMBODIMENTS

Example 1: Production of Maleimide-Functionalized BSA 250 mg BSA (Sigma-Aldrich, Cat. No. A7030) was dissolved in 5 ml of 1M sodium borate (pH 8.2). 6 mg of N-maleoyl-β-alanine (Sigma-Aldrich Cat. No. 63285) was added to the solution and it was incubated for 2 hours at room temperature. In addition, 130 mg of N-hydroxysuccinimide was dissolved in 730 µl acetonitrile. Then 96 mg of N-maleoyl-β-alanine was dissolved in 570 µl of the N-hydroxysuccinimide solution. 80 µl acetonitrile and 80 µl diisopropyl carbodiimide were added to this solution. After incubation for 5 minutes at room temperature, the mixture was centrifuged for 5 min. The supernatant was added dropwise to the BSA solution, stirring continuously. After incubation for 45 min at room temperature, the mixture was dialyzed four times against 500 ml PBS on ice, and then concentrated by ultrafiltration to a volume of 4 ml.

Example 2: Preparation of Maleimide-Functionalized PVA 120 mg of carbonyl diimidazole was dissolved in 3 ml of 4% (w/v) PVA in DMSO (Sigma, Cat. No. P8136) and was incubated for 3 h at room temperature. This solution was then added dropwise, with stirring, to 420 µl ethylene diamine, and stirred for 2 days at room temperature in a closed vessel. Aminated PVA was precipitated by adding 30 ml ethanol/diethyl ether (1:5) and pelletized by centrifugation. The pellet was dissolved in 3 ml PBS and adjusted to pH 6 by adding 2.5 M HCl. Then the solution was dialyzed three times against 1 liter of 100 mM sodium carbonate (pH 8.2). For functionalization of the aminated PVA, first 75 mg of N-maleoyl-β-alanine was dissolved in 1029 µl 1M N-hydroxysuccinimide in acetonitrile and was activated by adding 125 µl diisopropyl carbodiimide. After 10 min at room temperature, the mixture was centrifuged for 5 min and the supernatant was added dropwise to the stirred amine-PVA solution. After 1 h at room temperature, the mixture was centrifuged for 10 min at 3000 rpm and the supernatant was dialyzed three times against 600 ml PBS. Then the mixture was concentrated by ultrafiltration to 3.5 ml.

Instead of PVA, dextran can also be functionalized with maleimide or thiol groups. To prepare thiol-functionalized dextran, for example, first 1 g dextran (Serva, Cat. No. 18690) was dissolved in 10 ml anhydrous dimethylsulfoxide. In addition, 100 mg carbonyl diimidazole was dissolved in this solution. After incubation for 2 hours at room temperature, 1.12 g cystamine×2 HCl and 1.5 ml pyridine were added. For complete dissolution of the diamine, the mixture was treated for some minutes in an ultrasonic bath. After incubation for two days, the mixture was dialyzed three times against 1 liter $H_2O$ (regenerated cellulose membrane, MWCO 3000). During dialysis, the acid content was adjusted to pH 6 by adding HCl. Then 347 mg dithiothreitol was dissolved in the dialyzate. Immediately thereafter, modified dextran was separated from low-molecular components by gel filtration chromatography with Sephadex G25 (HiPrep™ 26/10 desalting column (GE Healthcare/Life Sciences) with 5 mM sodium phosphate (pH 5) and a flow rate of 10 ml/min. Dextran-containing fractions were combined (36 ml) and then purified further by dialysis first against 1 liter 1 mM HCl, and then against 1 liter 0.5 mM HCl under a nitrogen atmosphere. Finally the mixture was concentrated by lyophilization to 9 ml and separated from undissolved material by centrifugation.

Example 3: Coupling of Peptides and Gel Formation

Binding of peptides to maleimide-BSA: 10 µl of maleimide-BSA was incubated with various amounts of peptide HW1 (acetyl-KGLQGCGLQGK-OH; SEQ ID NO:1) or HW2 (acetyl-KGGLQGGK-OH; SEQ ID NO:2) at room temperature for at least 10 min in a volume of 12 µl. Then it was separated so that it was free from coupled peptide by gel filtration chromatography and the elution profile was determined by measuring the absorption at 214 nm. The chromatograms were integrated to determine the level of incorporation. Incorporation of 93% in maleimide-BSA was measured for HW1, and incorporation of 10% for HW2. However, no coupling of HW1 to unmodified BSA was detected.

Binding of peptides to maleimide-PVA: 4 µl maleimide-PVA or 2 µl 4% PVA was incubated with 100 nmol peptide HW1 (acetyl-KGLQGCGLQGK-OH; SEQ ID NO:1) or HW2 (acetyl-KGGLQGGK-OH; SEQ ID NO:2) at room temperature for at least 10 min in a volume of 16 µl. Then 20 µl of a 1:4 dilution was separated by gel filtration chromatography and the elution profile was determined by measuring the absorption at 214 nm. The chromatograms were integrated to determine the level of incorporation. Table 1 shows the relative proportion of unbound peptides:

TABLE 1

| | Incorporation of peptides | | | | | |
|---|---|---|---|---|---|---|
| Mal-PVA | ✓ | | ✓ | | | ✓ |
| PVA | | | | ✓ | | |
| HW1 | | ✓ | ✓ | ✓ | | |
| HW2 | | | | | ✓ | ✓ |
| Free peptide (%) | n/a | 100 | 12 | 96 | 100 | 107 |

Gel formation: Both materials could be converted to gels by adding a crosslinking agent with two thiol groups. Table 2 shows typical amounts that are suitable for gel formation in different strengths.

TABLE 2

| | Gel formation | | | | | |
|---|---|---|---|---|---|---|
| Maleimide-BSA (µl) | 308 | 167 | 178 | | | |
| Maleimide-PVA (µl) | | | | 308 | 168 | 100 |
| PBS (µl) | 0 | 167 | 178 | 0 | 168 | 300 |
| 100 mg/ml Dithio-PEG (3 kDa) (µl) | 92 | 66 | 54 | 92 | 64 | 50 |

Example 4: Adhesion of 3T3 Cells to Gel Components

In each case 1 µl of different components in a printing buffer (0.5% trehalose, 1 µg/ml BSA-tetramethyl rhodamine conjugate (Invitrogen, Carlsbad, Calif.; Cat. No. A-23016) in PBS (20 mM sodium phosphate (pH 7.2), 150 mM NaCl)) was applied to nitrocellulose-coated glass slides (NMI Technologietransfer GmbH, Reutlingen). The slides were stored overnight at room temperature and on the next day were injected with blocking solution (StabilGuard®, SurModics, Eden Prairie, Minn.) to block the areas between the components. Then the slides were washed twice with PBS and swirled with a cell suspension (105 3T3 cells per ml) for 2 hours. Then the cell suspension was removed, and the slides were treated with Coomassie dye solution and photographed.

The results for adhesion of 3T3 cells to gel components are shown in FIG. 1, using 200 µg/ml fibronectin in A, a 1:5-diluted maleimide-PVA solution in B, 1 µl of a solution consisting of 2 µl maleimide-PVA, 0.5 µl HW9 (FITC-β-ala-GCGYGRGDSPGSGC; SEQ ID NO:3 with fluorescein group in front of the β-alanine; 50 mM), 7.5 µl PBS in C, 20 mg/ml Dithio-PEG (3 kDa; Rapp-Polymere Tubingen; Cat. No. 11 3000-40) in D, 1:10-diluted maleimide-BSA in E, and 1 µl of a solution consisting of 2 µl maleimide-BSA, 0.38 µl HW9 (FITC-β-ala-GCGYGRGDSPGSGC; SEQ ID NO:3 with fluorescein group before the β-alanine; 50 mM), 7.62 µl PBS, in F.

Example 5: Cultivation of MDCK Cells in PVA Gel

MDCK cells (a canine kidney epithelial cell line) were sown in PVA gels at a density of 1 million cells/ml. (Composition of the gel: maleimide-PVA: 10 µl, PBS: 6 µl, MDCK cells: $10^4$ cells in 10 µl PBS, crosslinking agent (Dithio-PEG, 3 kDa; 100 mg/ml): 4 µl). The total volume of the individual gel was 30 µl, and 4 µl of crosslinking agent was put in the cell culture vessel (Nalge Nunc Int., LAB-TEK II, Chambered Coverglass—Borosilicate). Once the remaining gel mixture, which also contained the cells, had been prepared, the crosslinking agent was mixed with the gel components by pipetting in and out 3 times. A gel formed within approx. 10 seconds. The gel was covered with 400 µl of culture medium (DMEM High Glucose, 4 mM glutamine, 1% penicillin/streptomycin and 10% fetal calf serum) and was incubated at 5% $CO_2$ and 37° C. in a moist atmosphere. After cultivation of the cells in the PVA gel for 7 and 15 days, actin staining (TRITC-Phalloidin [0.3 µg/ml], Sigma) and nuclear staining (SYTO® Green [167 nM], Molecular Probes) was carried out for visualization of the MDCK cells.

Figure 1A:
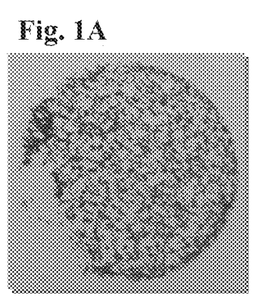
FIGS. 1A-F the results of adhesion tests of 3T3 cells on different gel components.
Figure 1B:
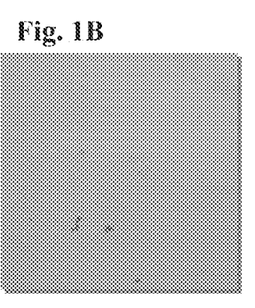
Figure 1C:
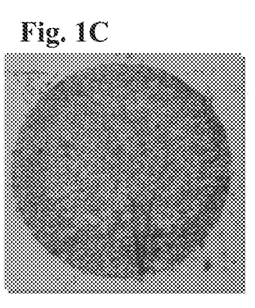
Figure 1D:
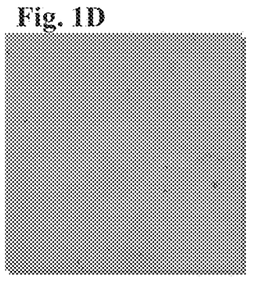
Figure 1E:
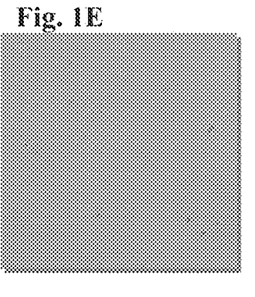
Figure 1F:
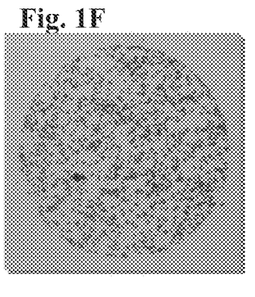
Figure 2A:
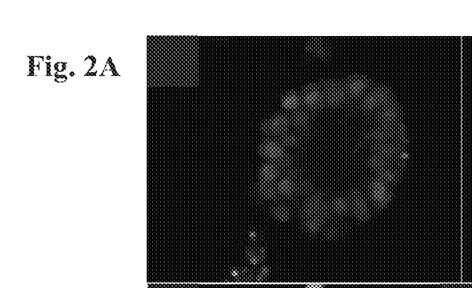
FIG. 2A shows nuclear staining with SYTO® Green.
Figure 2B:
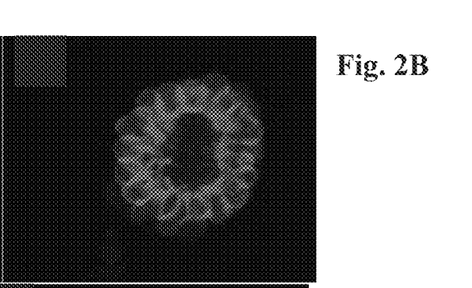
FIG. 2B shows actin staining with TRITC-Phalloidin.
Figure 2C:
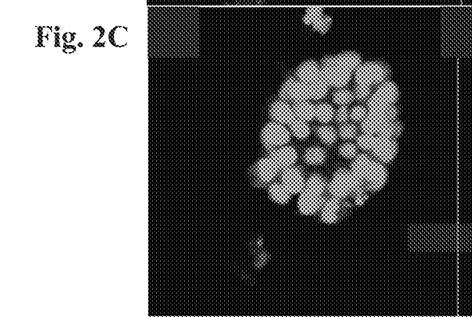
FIGS. 2C-F show optical sections in the outer region through an MCDK cyst in PVA gel in which lumen is not visible, with nuclear staining with SYTO® Green in FIG. 2C and actin staining with TRITC-Phalloidin in FIG. 2D.
Figure 2D:
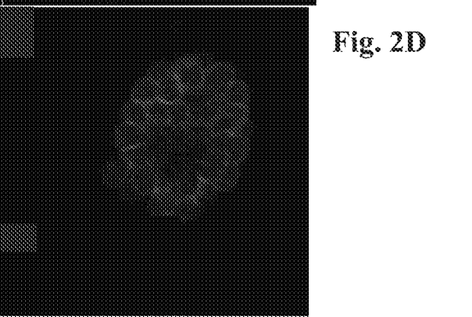
Figure 2E:
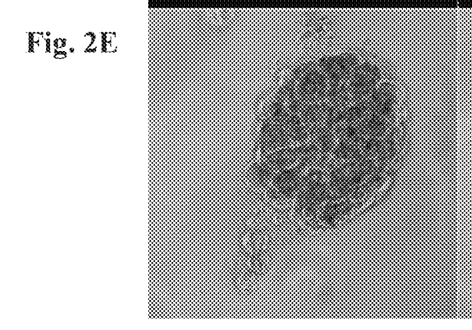
Figure 2F:
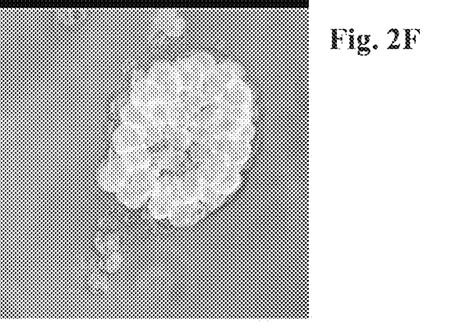

FIGS. 2A-F show confocal laser scanning micrographs of MDCK cysts after 15 days in the PVA gel. For the MDCK cyst shown in FIG. 2, the fluorescence labeling of the actin cytoskeleton suggests polarity of the cells with apical zone toward the lumen and basolateral zone toward the PVA matrix. FIGS. 2A-B show the optical section through an MDCK cyst in PVA gel for visualization of the lumen (confocal laser scanning microscopy): FIG. 2A: nuclear staining with SYTO® Green. FIG. 2B: actin staining with TRITC-Phalloidin. FIGS. 2C-F show the optical section in the outer region through an MDCK cyst in PVA gel, in which the lumen is not visible: FIG. 2C: nuclear staining with SYTO® Green. FIG. 2D: actin staining with TRITC-Phalloidin. FIG. 2C: phase-contrast photograph. FIG. 2D: overlay of C, D, and E.

Example 6: Cultivation of Mesenchymal Stem Cells in PVA and BSA Gels

2D-Cultivation of the cells: Human mesenchymal stem cells were cultivated by standard methods in tissue culture bottles (T75 bottles, Greiner), loosened from the surface with trypsin solution, pelletized, taken up in MSC medium and counted.

3D-Cultivation: For embedding cells in BSA gels, 21.6 µl of maleimide-BSA and 19 µl of cell suspension (50000 cells) were placed in a well of a microtiter plate and crosslinked by mixing-in 9.4 µl of crosslinking solution (100 mg/ml Dithio-PEG, 3,000 Da). For embedding in PVA, 15.1 µl of maleimide-PVA and 28.7 µl of cell suspension (50,000 cells) were placed in a well of a microtiter plate and crosslinked by mixing-in 6.2 µl of crosslinking solution. After approx. 5 min the gel preparations were covered with 250 µl of medium and cultivated for 6 days at 37° C. A calcein-propidium iodide staining was carried out and the gels were photographed in a fluorescence microscope. It was found that in both gels the majority of the cells (>95%) were still alive even after incubation for 6 days.

Figure 3A:
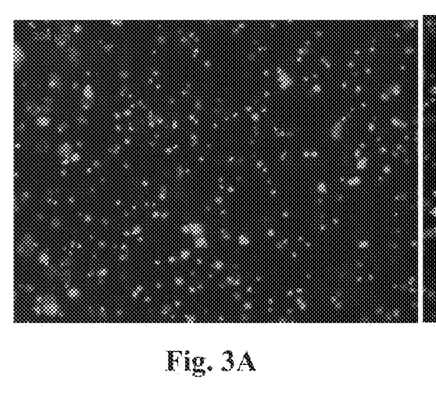
Figure 3B:
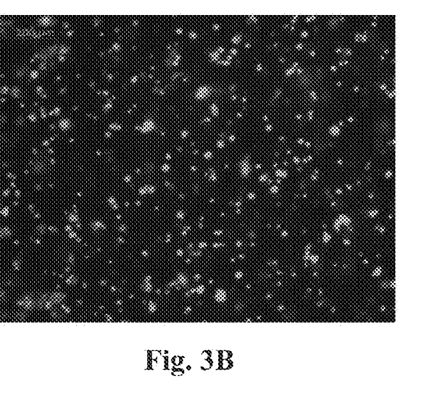

FIG. 3 shows the results of the calcein/propidium iodide staining of mesenchymal stem cells after 6 days of 3D cultivation: A: cells in BSA gel. B: cells in PVA gel.

Example 7: Examples of Cell Cultures in BSA and PVA Gels

Several primary cell preparations and cell lines were cultivated successfully in PVA and BSA gels. Table 3 gives an overview of these experiments.

TABLE 3

3D cell culture with different types of cells

| Cell type | Type of gel | Cultivation time (days) | Assays | Results |
| --- | --- | --- | --- | --- |
| Human chondrocytes from osteoarthritic cartilage | PVA | 16 | Calcein, propidium iodide | >80% survival |
| Human chondrocytes from osteoarthritic cartilage | BSA | 16 | Calcein, propidium iodide | >90% survival |
| Mouse MC3T3 cell line | PVA | 3 | Calcein, propidium iodide | >80% survival |
| Mouse MC3T3 cell line | BSA | 3 | Calcein, propidium iodide | >70% survival |
| Human mesenchymal stem cells | PVA | 6 | Calcein, propidium iodide | >95% survival |
| Human mesenchymal stem cells | BSA | 6 | Calcein, propidium iodide | >95% survival |
| MDCK | BSA | 6 | Phase-contrast microscopy | Formation of cysts |
| NIH 3T3 | PVA | 17 | Calcein, propidium iodide | >50% survival, formation of aggregates (size up to 60 µm) |
| MDCK | PVA | 17 | Calcein, propidium iodide | >50% survival, formation of cysts (size to 100 µm) |

TABLE 3-continued 3D cell culture with different types of cells

| Cell type | Type of gel | Cultivation time (days) | Assays | Results |
|---|---|---|---|---|
| MDCK | PVA | 7 and 15 | Visualization of the polarity of cysts by actin staining | Apical and basolateral zones visualized. For the cysts investigated, both polarities found: apical both toward lumen and toward matrix. |

It can be seen from the above results with the biomaterials tested that both the polymers used and the peptides used are excellent examples for the biomaterials according to the invention.

Therefore, what is claimed, is:

1. A hydrogel for the cultivation of a cell or tissue, comprising:
   a hydrophilic polymeric carrier, which comprises at least one crosslinkable hydrophilic polymer, wherein the polymer is functionalized with at least three maleimide groups which the non-functionalized polymer does not normally possess, and wherein the polymer is maleimide-serum albumin, and
   a crosslinking agent comprising at least two thiol groups, wherein the crosslinking agent is dithio-PEG having a molecular weight of 3 kDa, and wherein the dithio-PEG crosslinks the polymer via covalent bonding between the thiol groups of the dithio-PEG and the maleimide groups of the maleimide-serum albumin polymer.

2. The hydrogel of claim 1, wherein the polymer is crosslinkable in the presence of cells.

3. The hydrogel of claim 1, further comprising at least one biofactor.

4. The hydrogel of claim 1, wherein the polymer is aminated.

5. A method comprising:
   a) introducing a cell or tissue into the hydrogel of claim 1, and
   b) culturing the cell or tissue in the hydrogel.

6. The method of claim 5, wherein the polymer is aminated.

7. The method of claim 5, wherein the hydrogel further comprises a biofactor.

8. The method of claim 7, wherein the biofactor is selected from the group consisting of peptides, proteins, nucleic acids, organic active substances, apoptosis-inducing active substances, adhesion-promoting active substances, growth-inhibiting active substances, anti-inflammatory active substances, receptor agonists, receptor antagonists, proteins of the extracellular matrix, cell surface proteins, antibodies, growth factors, sugars, lectins, carbohydrates, cytokines, DNA, RNA, siRNA, aptamers, and fragments thereof that are relevant to binding or action, and mixtures thereof.

9. The method of claim 7, wherein the biofactor has at least one thiol group, via which the biofactor is bound to a maleimide group of the polymer.

10. The method of claim 5, wherein the polymer is crosslinked using thiol-functionalized PEG.

11. A hydrogel for the cultivation of a cell or tissue, comprising:
   a hydrophilic polymeric carrier, which comprises at least one crosslinkable hydrophilic polymer, wherein the polymer is functionalized with at least three maleimide groups which the non-functionalized polymer does not normally possess, and wherein the polymer is maleimide-serum albumin,
   a crosslinking agent comprising at least two thiol groups, wherein the crosslinking agent is dithio-PEG having a molecular weight of 3 kDa which crosslinks the polymer, and
   at least one biofactor, wherein the biofactor has at least one thiol group, via which the biofactor is bound to a maleimide group of the polymer.

12. The hydrogel of claim 11, wherein the biofactor is selected from the group consisting of peptides, proteins, nucleic acids, organic active substances, apoptosis-inducing active substances, adhesion-promoting active substances, growth-inhibiting active substances, anti-inflammatory active substances, receptor agonists, receptor antagonists, proteins of the extracellular matrix, cell surface proteins, antibodies, growth factors, sugars, lectins, carbohydrates, cytokines, DNA, RNA, siRNA, aptamers, and fragments thereof that are relevant to binding or action, and mixtures thereof.

13. The hydrogel of claim 11, wherein the polymer is aminated.

14. The hydrogel of claim 11, wherein the polymer is crosslinkable in the presence of cells.

15. A hydrogel for the cultivation of a cell or tissue, comprising:
   a hydrophilic polymeric carrier, which comprises at least one crosslinkable hydrophilic polymer, wherein the polymer is functionalized with at least three maleimide groups which the non-functionalized polymer does not normally possess, and wherein the polymer is maleimide-serum albumin or maleimide-PVA (polyvinyl alcohol), and
   a crosslinking agent comprising at least two thiol groups, wherein the crosslinking agent has a molecular weight of 3 kDa, and wherein the crosslinking agent crosslinks the polymer via covalent bonding between the thiol groups of the crosslinking agent and the maleimide groups of the maleimide-serum albumin polymer or maleimide-PVA polymer.

16. A hydrogel for the cultivation of a cell or tissue, comprising:
   a hydrophilic polymeric carrier, which comprises at least one crosslinkable hydrophilic polymer, wherein the polymer is functionalized with at least three maleimide groups which the non-functionalized polymer does not normally possess, and wherein the polymer is maleimide-serum albumin or maleimide-PVA, and
   a crosslinking agent comprising at least two thiol groups, wherein the crosslinking agent is dithio-PEG and has a molecular weight of 3 kDa, and wherein the crosslinking agent crosslinks the polymer via covalent bonding between the thiol groups of the crosslinking agent and the maleimide groups of the maleimide-serum albumin polymer or maleimide-PVA polymer.

17. The hydrogel of claim 16, further comprising at least one biofactor, wherein the biofactor has at least one thiol group, via which the biofactor is bound to a maleimide group of the polymer, wherein the biofactor comprises a polypeptide sequence selected from the group consisting of SEQ ID NO: 1, SEQ ID NO: 2, and SEQ ID NO: 3.

18. The hydrogel of claim 16, further comprising at least one biofactor, wherein the biofactor has at least one thiol group, via which the biofactor is bound to a maleimide group of the polymer, wherein the biofactor is peptide HW1 (acetyl-KGLQGCGLQGK-OH).

19. The hydrogel of claim 16, further comprising at least one biofactor, wherein the biofactor has at least one thiol group, via which the biofactor is bound to a maleimide group of the polymer, wherein the biofactor is peptide HW2 (acetyl-KGGLQGGK-OH).

20. The hydrogel of claim 16, further comprising at least one biofactor, wherein the biofactor has at least one thiol group, via which the biofactor is bound to a maleimide group of the polymer, wherein the biofactor is peptide HW9 (FITC-β-Ala-GCGYGRGDSPGSGC).

21. The hydrogel of claim 16, further comprising at least one cell to be cultivated in the hydrogel, wherein the cell is selected from the group consisting of a human chondrocyte from osteoarthritic cartilage, a human mesenchymal stem cell, a human epithelial cell, and a human fibroblast.

22. A hydrogel for the cultivation of a cell or tissue, comprising:
- a hydrophilic polymeric carrier, which comprises at least one crosslinkable hydrophilic polymer, wherein the polymer is functionalized with at least three maleimide groups which the non-functionalized polymer does not normally possess, and wherein the polymer is maleimide-serum albumin,
- a crosslinking agent comprising two thiol groups, wherein the crosslinking agent is dithio-PEG and has a molecular weight of 3 kDa, and wherein the crosslinking agent crosslinks the polymer via covalent bonding between the two thiol groups of the crosslinking agent and the maleimide groups of the maleimide-serum albumin polymer.

* * * * *